(12) United States Patent
Takato

(10) Patent No.: US 12,181,654 B2
(45) Date of Patent: Dec. 31, 2024

(54) ENDOSCOPE OBJECTIVE OPTICAL SYSTEM AND ENDOSCOPE

(71) Applicant: OLYMPUS CORPORATION, Hachioji (JP)

(72) Inventor: Hideyasu Takato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 584 days.

(21) Appl. No.: 17/488,400

(22) Filed: Sep. 29, 2021

(65) Prior Publication Data
US 2022/0019072 A1   Jan. 20, 2022

Related U.S. Application Data

(63) Continuation of application No. PCT/JP2019/017866, filed on Apr. 26, 2019.

(51) Int. Cl.
*G02B 23/24* (2006.01)
*A61B 1/00* (2006.01)
*G02B 9/12* (2006.01)

(52) U.S. Cl.
CPC ........ *G02B 23/243* (2013.01); *A61B 1/00096* (2013.01); *G02B 9/12* (2013.01)

(58) Field of Classification Search
CPC .................................................. G02B 23/243
See application file for complete search history.

(56) References Cited

U.S. PATENT DOCUMENTS 4,059,344 A   11/1977 Yamasita
8,203,798 B2   6/2012 Takato 9,568,726 B2   2/2017 Kamo et al.
9,817,226 B2   11/2017 Noguchi
10,437,039 B2   10/2019 Sasamoto
(Continued)

FOREIGN PATENT DOCUMENTS

JP   S5149734 A   4/1976
JP   4819969 B2   9/2011
(Continued)

OTHER PUBLICATIONS

Melles Griot, "Lens Shape" and "Aberration Balancing", 1999 (Year: 1999).*
(Continued)

*Primary Examiner* — Christopher Stanford
(74) *Attorney, Agent, or Firm* — Holtz, Holtz & Volek PC

(57) ABSTRACT

An endoscope objective optical system includes, in order from an object side, a first group having a negative refractive power, a second group having a positive refractive power, and a third group having a positive refractive power. Focusing from an object point at a long distance to an object point at a short distance is carried out by moving the second group from the object side to an image side. The first group includes a lens having a negative refractive power, the second group includes a lens which is a meniscus lens having a positive refractive power of which a convex surface is directed toward the image side, and the third group includes, in order from the object side, a lens having a positive refractive power, and a cemented lens composed of a lens having a positive refractive power and a lens having a negative refractive power.

2 Claims, 11 Drawing Sheets

(56) References Cited

U.S. PATENT DOCUMENTS

| | | |
|---|---|---|
| 2011/0211267 A1 | 9/2011 | Takato |
| 2016/0238832 A1 | 8/2016 | Sasamoto |
| 2016/0327780 A1 | 11/2016 | Kamo et al. |
| 2017/0071449 A1 | 3/2017 | Noguchi |
| 2017/0235123 A1* | 8/2017 | Kamo ................ G02B 23/243 359/738 |
| 2019/0261834 A1 | 8/2019 | Kawakami |

FOREIGN PATENT DOCUMENTS

| | | |
|---|---|---|
| JP | 5930257 B1 | 5/2016 |
| JP | 6001229 B2 | 9/2016 |
| JP | 2017219783 A | 12/2017 |
| WO | 2015064614 A1 | 5/2015 |
| WO | 2018116865 A1 | 6/2018 |

OTHER PUBLICATIONS

International Search Report (ISR) dated Jul. 23, 2019, issued in International Application No. PCT/JP2019/017866.
Written Opinion dated Jul. 23, 2019, issued in International Application No. PCT/JP2019/017866.
International Preliminary Report on Patentability (IPRP) and English translation thereof dated Nov. 4, 2021, Issued in International Application No. PCT/JP2019/017866.

* cited by examiner

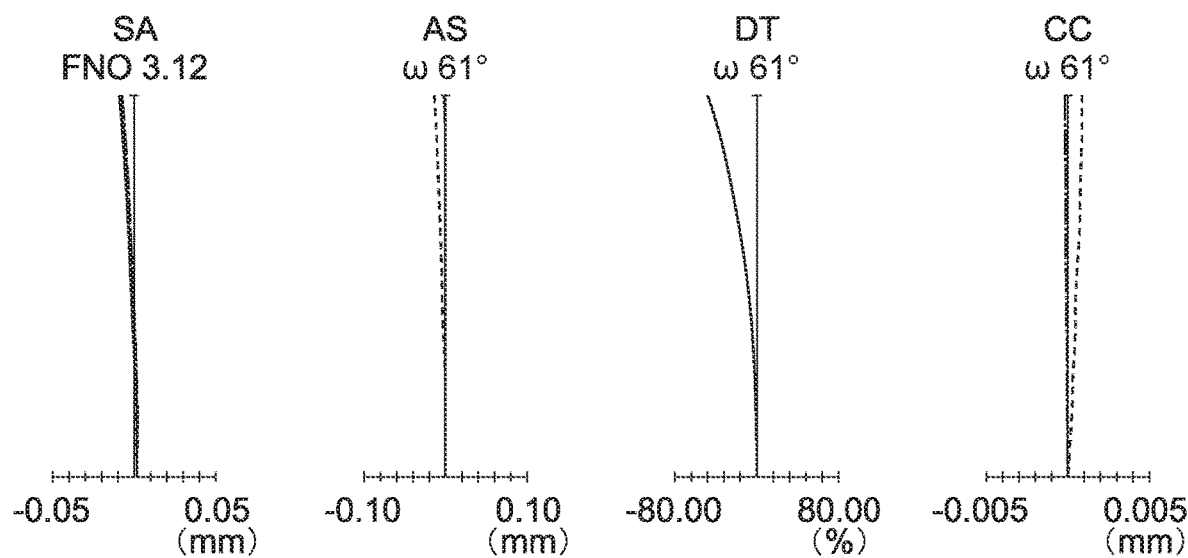
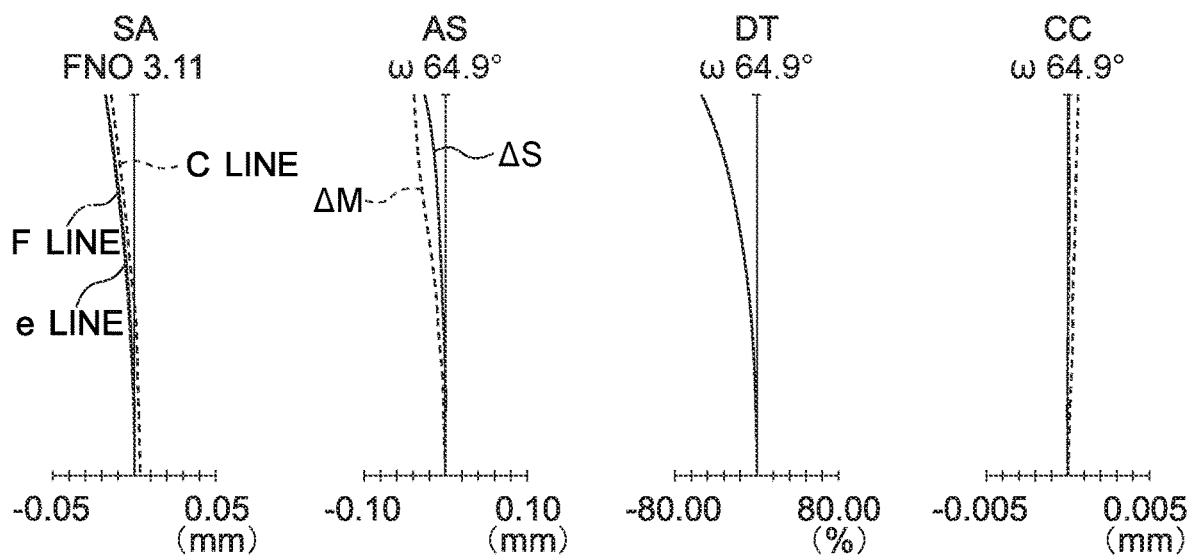

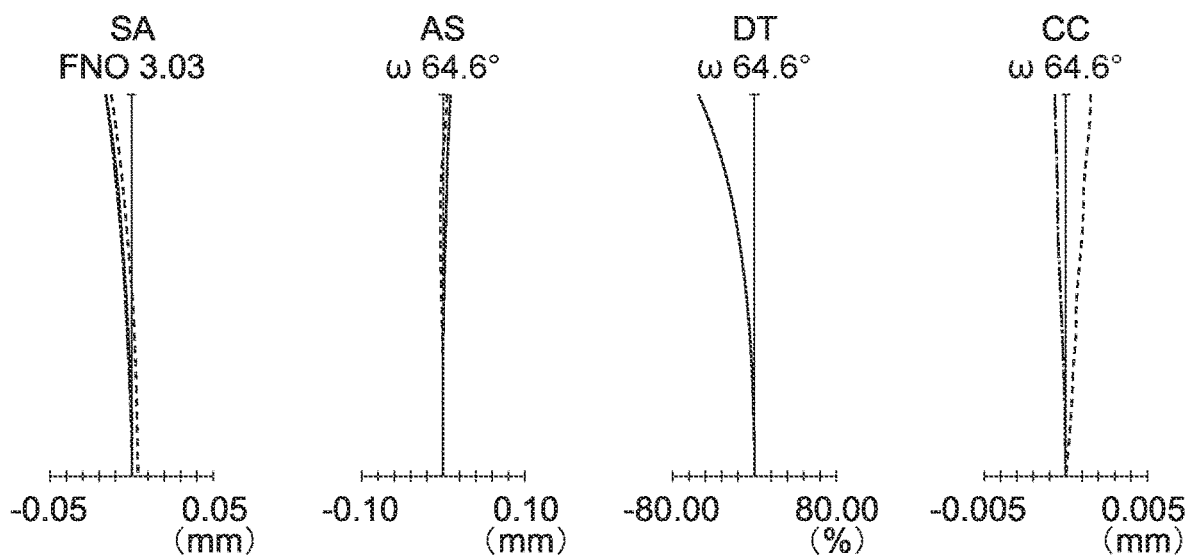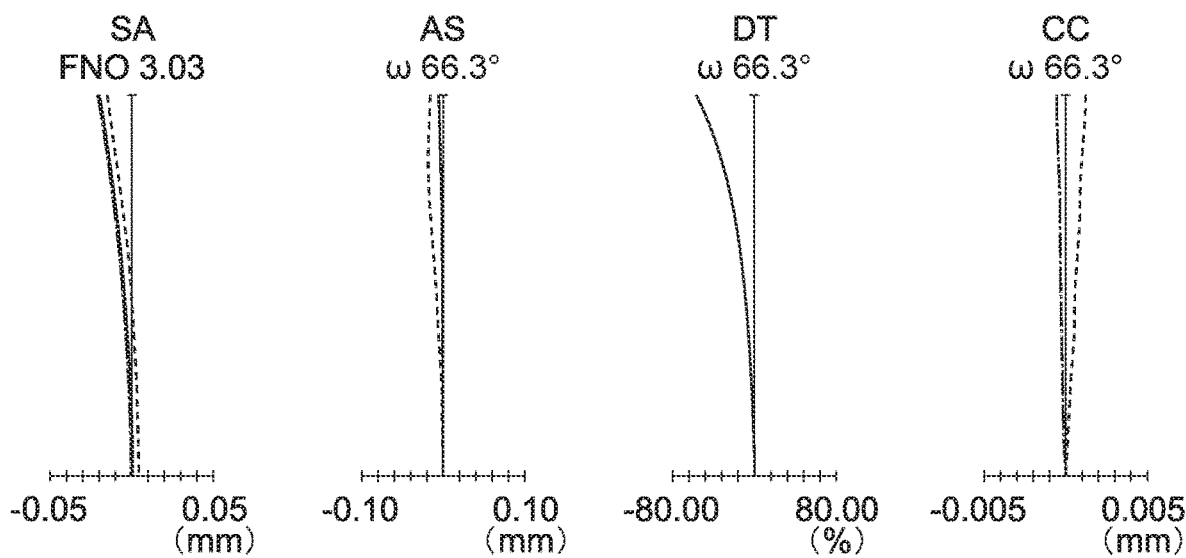

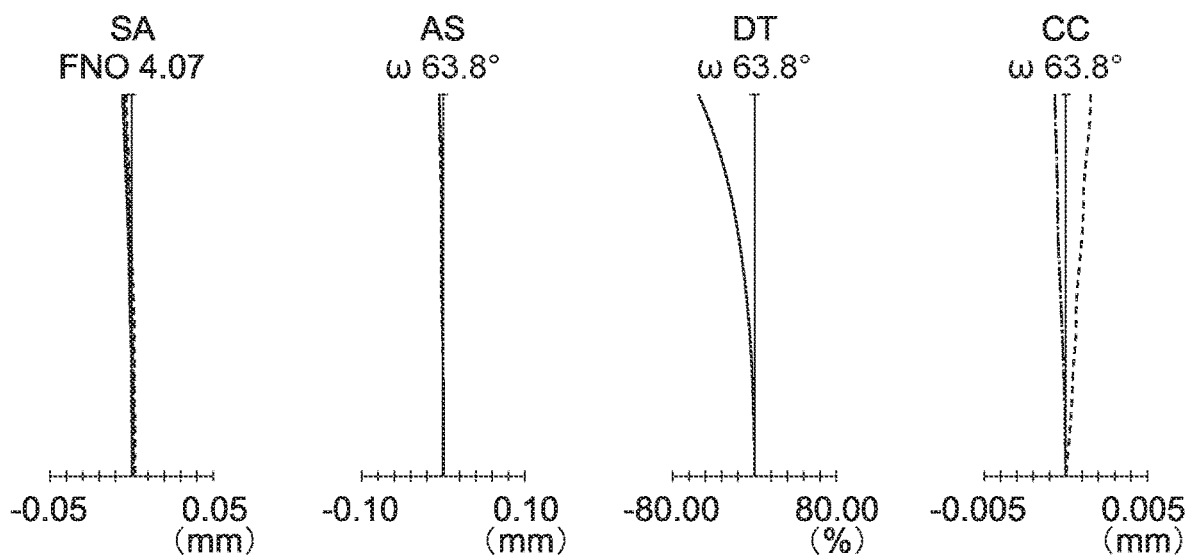
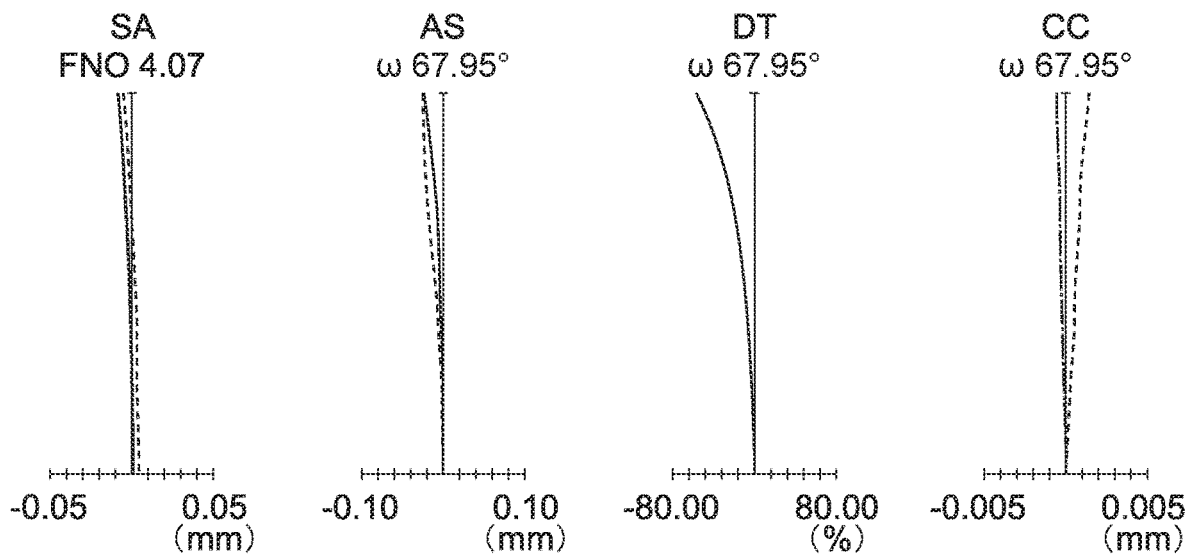

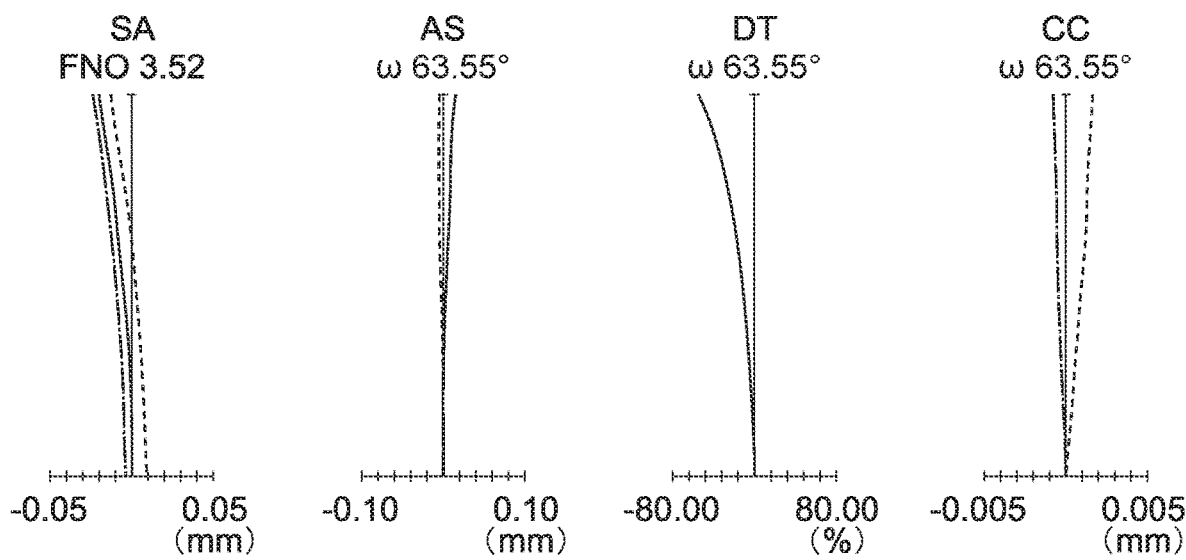
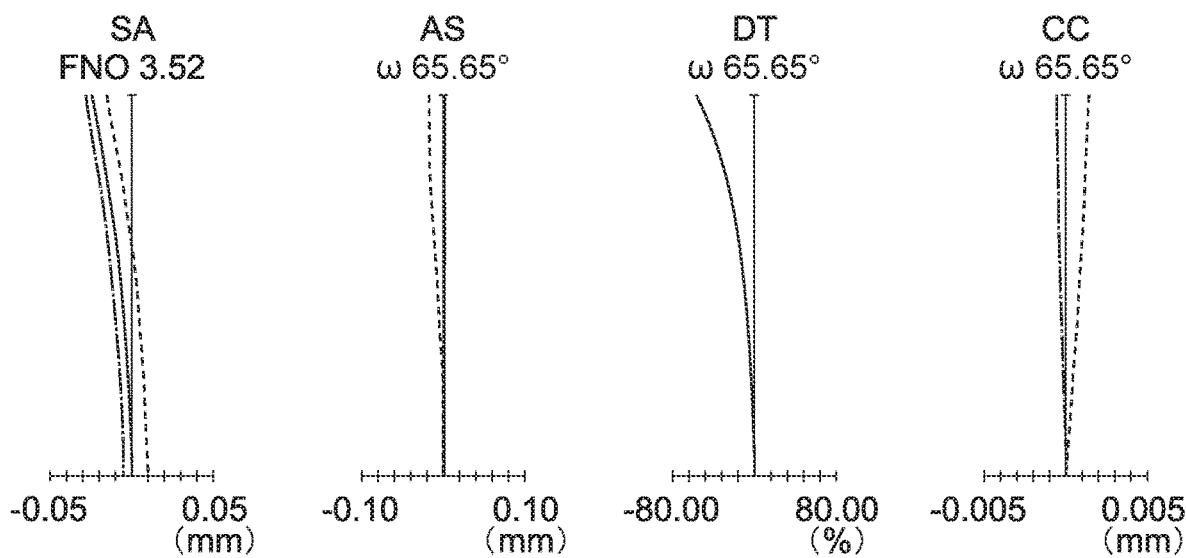

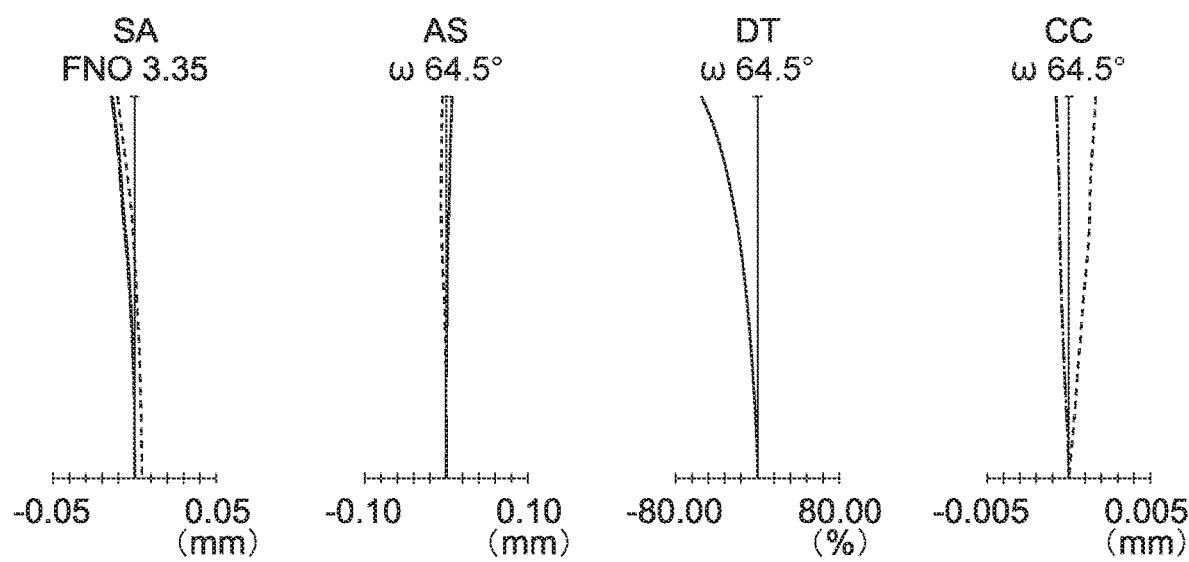
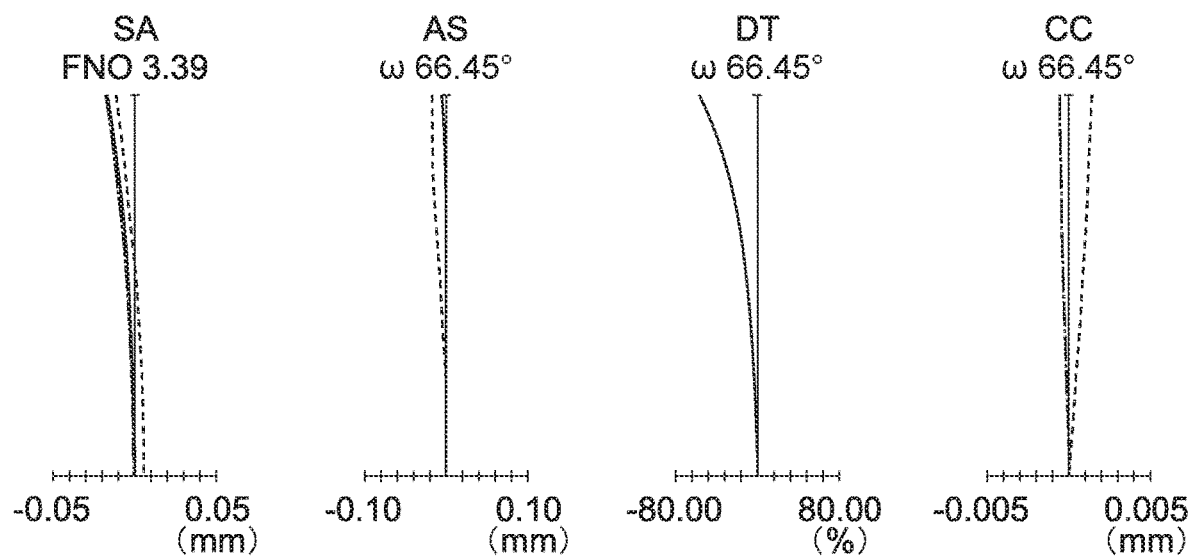

ENDOSCOPE OBJECTIVE OPTICAL SYSTEM AND ENDOSCOPE

CROSS-REFERENCE TO RELATED APPLICATION

The present application is a continuation application of PCT/JP2019/017866 filed on Apr. 26, 2019, the entire contents of which are incorporated herein by reference.

BACKGROUND

Technical Field

The disclosure relates to an optical system which has a focusing function, and particularly to an endoscope objective optical system and an endoscope which enable a close observation, or near-field observation, and relates to an endoscope using the same.

Description of the Related Art

In recent years, it is desired that a nasal endoscope for which the market has been expanding in a field of medical endoscopes, has a small diameter as a scope. For this, it is desirable that an objective system which is to be installed in a nasal endoscope also has a small size. Furthermore, nowadays, even in a nasal endoscope in which a small diameter is sought, a market needs of improving further an observation performance by installing a focusing function, not to mention a high image quality, have been increasing. Endoscope objective optical systems having such focusing function are proposed in Japanese Patent Publication No. 4819969, Japanese Patent Publication No. 5930257, Japanese Patent Publication No. 6001229, and Japanese Patent Application Laid-open Publication No. 2017-219783.

SUMMARY

An endoscope objective optical system according to at least some embodiments of the disclosure includes in order from an object side, a first group having a negative refractive power, a second group having a positive refractive power, and a third group having a positive refractive power, wherein focusing from an object point at a long distance to an object point at a short distance is carried out by moving the second group from the object side to an image side, the first group includes a lens having a negative refractive power, the second group includes a lens which is a meniscus lens having a positive refractive power of which a convex surface is directed toward the image side, the third group includes in order from the object side, a lens having a positive refractive power, and a cemented lens of a lens having a positive refractive power and a lens having a negative refractive power, and following conditional expressions (1″), (2), and (3) are satisfied.

$$8 < G2f/FL \leq 17.041 \quad (1'')$$

$$-0.16 < G1f/G2f < -0.04 \quad (2)$$

$$0 \leq (R3-R4)/(R3+R4) < 0.2 \quad (3)$$

where,

FL denotes a focal length of the overall endoscope objective optical system at the time of a far-point observation, G1f denotes a focal length of the first group, G2f denotes a focal length of the second group, R3 denotes a radius of curvature of an object-side surface of the lens which is a meniscus lens, and R4 denotes a radius of curvature of an image-side surface of the lens which is a meniscus lens.

Moreover, an endoscope according to at least some embodiments of disclosure includes the abovementioned endoscope objective optical system.

BRIEF DESCRIPTION OF THE DRAWINGS

FIG. 3A, FIG. 3B, FIG. 3C, and FIG. 3D show a spherical aberration (SA) in the normal observation state, an astigmatism (AS) in the normal observation state, a distortion (DT) in the normal observation state, and a chromatic aberration of magnification (CC) in the normal observation state respectively, of the endoscope objective optical system according to the example 1, and FIG. 3E, FIG. 3F, FIG. 3G, and FIG. 3H show a spherical aberration (SA) in the close observation state, an astigmatism (AS) in the close observation state, a distortion (DT) in the close observation state, and a chromatic aberration of magnification (CC) in the close observation state respectively, of the endoscope objective optical system according to the example 1;

FIG. 5A, FIG. 5B, FIG. 5C, and FIG. 5D show a spherical aberration (SA) in the normal observation state, an astigmatism (AS) in the normal observation state, a distortion (DT) in the normal observation state, and a chromatic aberration of magnification (CC) in the normal observation state respectively, of the endoscope objective optical system according to the example 2, and FIG. 5E, FIG. 5F, FIG. 5G, and FIG. 5H show a spherical aberration (SA) in the close observation state, an astigmatism (AS) in the close observation state, a distortion (DT) in the close observation state, and a chromatic aberration of magnification (CC) in the close observation state respectively, of the endoscope objective optical system according to the example 2;

FIG. 7A, FIG. 7B, FIG. 7C, and FIG. 7D show a spherical aberration (SA) in the normal observation state, an astigmatism (AS) in the normal observation state, a distortion (DT) in the normal observation state, and a chromatic aberration of magnification (CC) in the normal observation state respectively, of the endoscope objective optical system according to the example 3, and FIG. 7E, FIG. 7F, FIG. 7G, and FIG. 7H show a spherical aberration (SA) in the close observation state, an astigmatism (AS) in the close observation state, a distortion (DT) in the close observation state, and a chromatic aberration of magnification (CC) in the close observation state respectively, of the endoscope objective optical system according to the example 3;

FIG. 9A, FIG. 9B, FIG. 9C, and FIG. 9D show a spherical aberration (SA) in the normal observation state, an astigmatism (AS) in the normal observation state, a distortion (DT) in the normal observation state, and a chromatic aberration of magnification (CC) in the normal observation state respectively, of the endoscope objective optical system according to the example 4, and FIG. 9E, FIG. 9F, FIG. 9G, and FIG. 9H show a spherical aberration (SA) in the close observation state, an astigmatism (AS) in the close observation state, a distortion (DT) in the close observation state, and a chromatic aberration of magnification (CC) in the close observation state respectively, of the endoscope objective optical system according to the example 4;

FIG. 11A, FIG. 11B, FIG. 11C, and FIG. 11D show a spherical aberration (SA) in the normal observation state, an astigmatism (AS) in the normal observation state, a distortion (DT) in the normal observation state, and a chromatic aberration of magnification (CC) in the normal observation state respectively, of the endoscope objective optical system according to the example 5, and FIG. 11E, FIG. 11F, FIG. 11G, and FIG. 11H show a spherical aberration (SA) in the close observation state, an astigmatism (AS) in the close observation state, a distortion (DT) in the close observation state, and a chromatic aberration of magnification (CC) in the close observation state respectively, of the endoscope objective optical system according to the example 5.

DETAILED DESCRIPTION

Embodiment

An endoscope objective optical system according to an embodiment will be described below by referring to the accompanying diagrams. However, the disclosure is not restricted to the embodiment below. A normal observation state refers to a state of observing an object point at a long distance, at the time of a far-point observation. Moreover, a close observation state refers to a state of observing an object point at a short distance, at the time of a near-point observation.

Figure 1A:
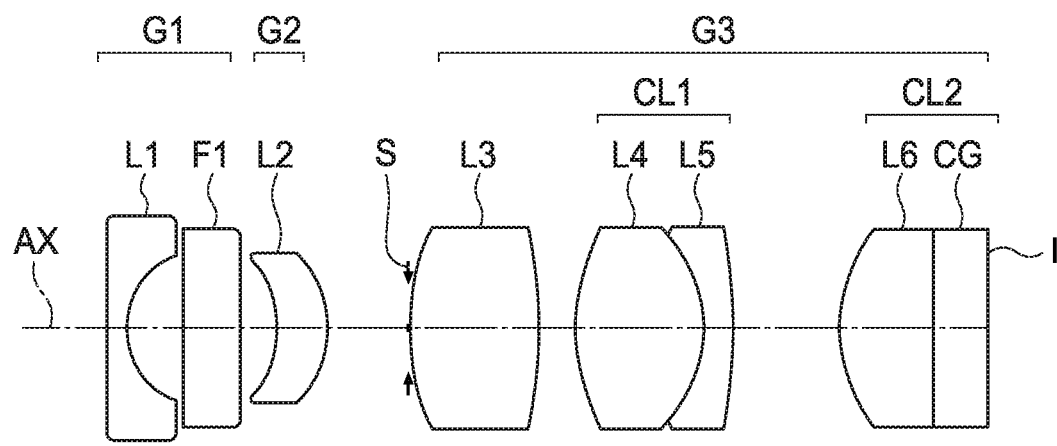
FIG. 1A is a cross-sectional view of a lens arrangement in a normal observation state of an endoscope objective optical system according to an embodiment.
Figure 1B:
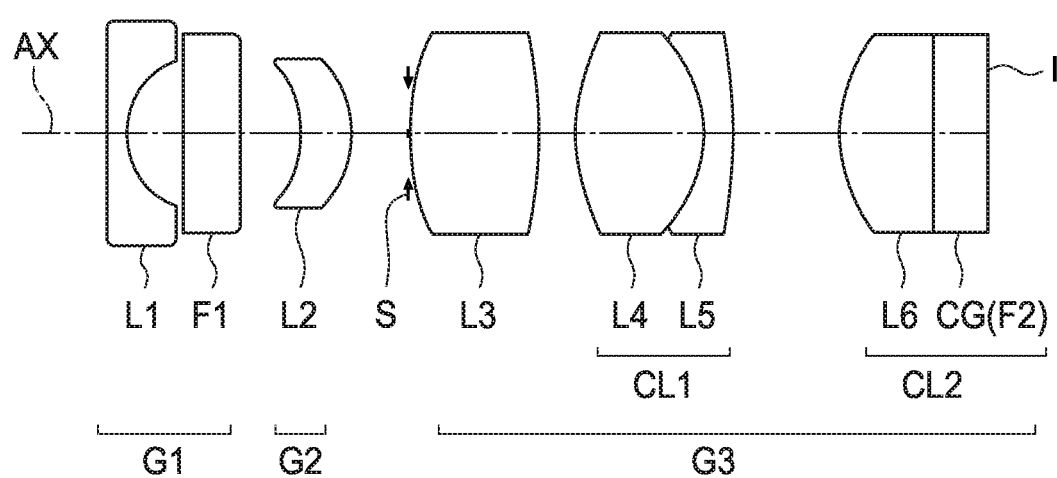
FIG. 1B is a cross-sectional view of a lens arrangement in a close observation state of the endoscope objective optical system according to the embodiment.

FIG. 1A is a cross-sectional view of a lens arrangement in a normal observation state of an endoscope objective optical system according to the embodiment. FIG. 1B is a cross-sectional view of a lens arrangement in a close observation state of the endoscope objective optical system according to the embodiment.

The endoscope objective optical system includes in order from an object side a first group G1 having a negative refractive power, a second group G2 having a positive refractive power, an aperture stop S, and a third group G3 having a positive refractive power.

In the endoscope objective optical system according to the embodiment, the first group G1 having a negative refractive power includes a first lens L1 having a negative refractive power. The second group G2 having a positive refractive power includes a second lens L2 which is a meniscus lens having a positive refractive power of which a convex surface directed toward an image side. The third group G3 having a positive refractive power includes in order from the object side, a third lens L3 having positive refractive power, a fourth lens L4 having a positive refractive power, a fifth lens L5 having a negative refractive power, and a sixth lens L6 having a positive refractive power. The fourth lens L4 having a positive refractive power and the fifth lens L5 having a negative refractive power are cemented, and form a cemented lens CL1. The sixth lens L6 having a positive refractive power is cemented to a cover glass CG of an image pickup surface (image plane I), and form a cemented lens CL2.

Focusing is carried out by moving the second group G2 toward the image side along an optical axis AX.

The aperture stop S is disposed between the second group G2 and the third group G3. The aperture stop S is fixed to the third group G3 at the time of focusing.

Moreover, a first plane parallel plate F1 is disposed on the image side (rear side) of the first lens L1 having a negative refractive power in the first group G1. The first plane parallel plate F1 is an infrared cut filter or a filter for cutting off laser light. It is possible to dispose the first plane parallel plate F1 at an arbitrary position in the endoscope objective optical system. Moreover, an image sensor which is not shown in the diagram is disposed near the image plane I of the endoscope objective optical system.

Reasons for and effects of adopting such arrangement in the present embodiment will be described below.

For reducing a size of the endoscope objective optical system and forming a movable lens group, it is desirable to make an arrangement such that the endoscope objective optical system includes in order from the object side, the first group G1 having a negative refractive power, the second group G2 having a positive refractive power, and the third group G3 having a positive refractive power.

Moreover, for reducing the size of the endoscope objective optical system and securing a space for the movement of a lens, a large space becomes necessary on the image side (rear side) of the movable group. Furthermore, it is necessary to secure a space for disposing the third group G3 and a back focus for a focal position adjustment.

Therefore, it is desirable that the second lens L2 has a shape of a meniscus lens having a positive refractive power of which a convex surface directed toward the image side. By making such shape, it is possible to bring a principal-point position of the second group G2 on the image side (rear side). Accordingly, it is possible to secure an area for the movement of the second lens L2, and the space on the image side (rear side) thereof.

Moreover, for shortening the overall length of lenses of the endoscope objective optical system, the number of lenses has to be made as small as possible. Therefore, in the present embodiment, each of the first group G1 and the second group G2 includes one lens. Here, the reference to 'lens' excludes a plane parallel plate. Moreover, the second group G2 is set to be the movable group, and a large surface space (an air space) is formed on the rear side of the second group G2. However, when such arrangement is made, aberrations occurred in the first group G1 and the second group G2 remain as they are. Therefore, the third group G3 is arranged such that at least a single lens having a positive refractive power and a cemented lens are used. By such arrangement, even with a substantial constraint of diameter and a constraint of overall length, it is possible to maintain a spherical aberration correction and a chromatic aberration correction to be favorable. Consequently, it is possible to achieve an endoscope objective optical system having a favorable performance for various aberrations.

Furthermore, the sixth lens L6 having a positive refractive power may be disposed leaving an air space, on the rear side of the image side of the cemented lens. The sixth lens L6 having a positive refractive power also assumes a function of a cover glass CG affixed to the image pickup surface I. Therefore, a position adjustment of the image plane is to be carried out by adjusting the air space between the cemented lens CL1 and the sixth lens L6 having a positive refractive power. Since it is possible to impart a refractive power even to an image pickup side, there is an advantage that an error sensitivity of the position adjustment of the image plane becomes small. At the time of adjusting the position of the image plane, it is possible to make small a shift in an image plane position.

The aperture stop S is disposed on the object side (front side) of the third group G3. However, when in an optical path between the second group G2 and the third group G3, whichever position the aperture stop S is disposed at, there is no substantial difference in a brightness and an optical performance. As to at which position the aperture stop S is to be disposed is determined according to an arrangement of a lens barrel for holding an endoscope objective optical system. At this time, the arrangement may be made such that the aperture stop S is disposed on the image side (rear side) of the second group G2, and is moved integrally with the second lens L2 which is a meniscus lens, at the time of focusing.

It is desirable that following conditional expression (1) is satisfied.

$$8 < G2f/FL < 35 \tag{1}$$

where,

G2f denotes a focal length of the second group G2, and

FL denotes a focal length of the overall endoscope objective optical system at the time of a far-point observation.

Conditional expression (1) is related to the focal length of the second group G2. The second group G2 moves along the optical axis AX in accordance with a change in an object-point distance, and bears a function of focusing for adjusting a position of the image plane. The second group G2, according to a structure of a frame forming such movable lens group, has a clearance of a moving frame and a fixed frame. Therefore, in the second group G2, an amount of decentering of a lens becomes large as compared to that in a fixed lens group.

In a case in which the refractive power of the movable lens group is large, it is necessary to suppress the amount of movement of decentering when the lens driven to be as small as possible by making the clearance of the frames small. For this, it is desirable that the refractive power of the second group G2 which is a driven lens satisfies conditional expression (1).

When a value falls below a lower limit value of conditional expression (1), the refractive power becomes small, and although it is possible to reduce the error sensitivity due to the decentering, it is not preferable, as the amount of movement becomes excessively large.

When an upper limit value of conditional expression (1) is exceeded, the refractive power of the second group G2 becomes excessively large, and therefore, a degradation of performance with respect to the decentering of the frames becomes remarkable.

Moreover, it is more preferable that conditional expression (1') is satisfied instead of conditional expression (1).

$$8 < G2f/FL < 28 \tag{1'}$$

When the endoscope objective optical system of the present embodiment satisfies conditional expression (1'), it is possible to make the degradation with respect to the decentering of the frames as small as possible.

Moreover, it is desirable that following conditional expression (2) is satisfied.

$$-0.16 < G1f/G2f < -0.04 \tag{2}$$

where,

G1f denotes a focal length of the first group G1, and

G2f denotes the focal length of the second group G2.

Conditional expression (2) is related to an appropriate ratio of a refractive power of the first group G1 and the refractive power of the second group G2. Conditional expression (2) can contribute to reducing the size of the overall endoscope objective optical system while correcting various aberrations favorably.

When a value falls below a lower limit value of conditional expression (2), the refractive power of the first group G1 becomes excessively small, and a height of a light ray incident on the first lens L1 becomes large. Consequently, this causes a diameter of the first lens L1 to become large.

When an upper limit value of conditional expression (2) is exceeded, the refractive power of the first group G1 becomes excessively large. Consequently, a focal position by the first group G1 moves to an image plane side. As a result, the overall length of the endoscope objective optical system becomes long, and the overall endoscope objective optical system becomes large in size. Furthermore, Petzval sum becomes large. Accordingly, there is an excessive correction of a curvature of field, and therefore, it is not preferable.

Moreover, according to a preferable aspect of the present embodiment, it is desirable that following conditional expression (3) is satisfied.

$$0 \le (R3-R4)/(R3+R4) < 0.2 \tag{3}$$

where,

R3 denotes a radius of curvature of an object-side surface of the second lens L2 which is a meniscus lens, and R4 denotes a radius of curvature of an image-side surface of the second lens L2 which is a meniscus lens.

Conditional expression (3) is related to a shape (shape factor) of the second lens L2 which is a meniscus lens.

When a value falls below a lower limit value of conditional expression (3), a longitudinal chromatic aberration becomes large, and it is not preferable.

When an upper limit value of conditional expression (3) is exceeded, the positive (convex) refractive power of the second lens L2 which is a meniscus lens becomes large. Consequently, the image plane is inclined toward an under side, and therefore it is not preferable.

Moreover, according to a preferable aspect of the present embodiment, it is desirable that following conditional expression (4) is satisfied.

$$0.1 < V2/FL < 0.4 \tag{4}$$

where,

V2 denotes an amount of movement of the second group G2 at the time of focusing from an object point at a long distance to an object point at a short distance, and FL denotes the focal length of the overall endoscope objective optical system at the time of a far-point observation.

Conditional expression (4) is related to the amount of movement of the second group G2. In an endoscope objective optical system having a movable group as in the present embodiment, for reducing the size and improving the performance, an amount of movement of the movable group becomes significant. Therefore, it is desirable that the endoscope objective optical system according to the present embodiment satisfies conditional expression (4).

When a value falls below a lower limit value of conditional expression (4), securing the amount of movement of the second group G2 becomes difficult, and the error sensitivity of the image-plane position with respect to the amount of movement of a lens becomes high, and therefore it is not preferable.

When an upper limit value of conditional expression (4) is exceeded, a space between the first group G1 and the second group G2 becomes large, and it is possible to secure the amount of movement of the second group G2. However, because the overall length of the endoscope objective optical system becomes excessively long, there is a possibility that an optical system becomes large in size.

Moreover, according to a preferable aspect of the present embodiment, it is desirable that following conditional expression (5) is satisfied.

$$-1.2 < f31/f32 < -0.7 \quad (5)$$

where, f31 denotes a focal length of the fourth lens L4 having a positive refractive power which forms the cemented lens CL1 in the third group G3, and f32 denotes a focal length of the fifth lens L5 having a negative refractive power which forms the cemented lens CL1 in the third group G3.

Conditional expression (5) is related to an appropriate ratio of f31 and f32.

When a value falls below a lower limit value of conditional expression (5), both the longitudinal chromatic aberration and a chromatic aberration of magnification are corrected inadequately for a C-line (656.27 nm) and are corrected excessively for an F-line (486.13 nm). Consequently, it becomes difficult to correct the chromatic aberration.

When an upper limit value of conditional expression (5) is exceeded, both the longitudinal chromatic aberration and the chromatic aberration of magnification are corrected excessively for the C-line, and are corrected inadequately for the F-line. Consequently, it becomes difficult to correct the chromatic aberration.

Moreover, it is more preferable that a conditional expression (5') is satisfied instead of conditional expression (5).

$$-1.05 < f31/f32 < -0.85 \quad (5')$$

Within a range of conditional expression (5'), it is possible to correct the chromatic aberration more favorably.

Moreover, according to a preferable aspect of the present embodiment, it is desirable that following conditional expression (6) is satisfied.

$$2.5 < G3f/FL < 4.5 \quad (6)$$

where,

G3f denotes a focal length of the third group G3, and

FL denotes the focal length of the overall endoscope objective optical system at the time of far-point observation.

Conditional expression (6) is related to correction of the curvature of field.

When a value falls below a lower limit value of conditional expression (6), the image plane is inclined toward an under side.

When an upper limit value of conditional expression (6) is exceeded, the image plane is inclined toward an over side. Consequently, an image is not focused at a central portion and a peripheral portion of a screen, and therefore it is not preferable.

Moreover, it is more preferable that conditional expression (6') is satisfied instead of conditional expression (6).

$$3 < G3f/FL < 4 \quad (6')$$

Within a range of conditional expression (6'), correction of the curvature of field becomes even more favorable.

Example 1

An endoscope objective optical system according to an example 1 will be described below.

Figure 2A:
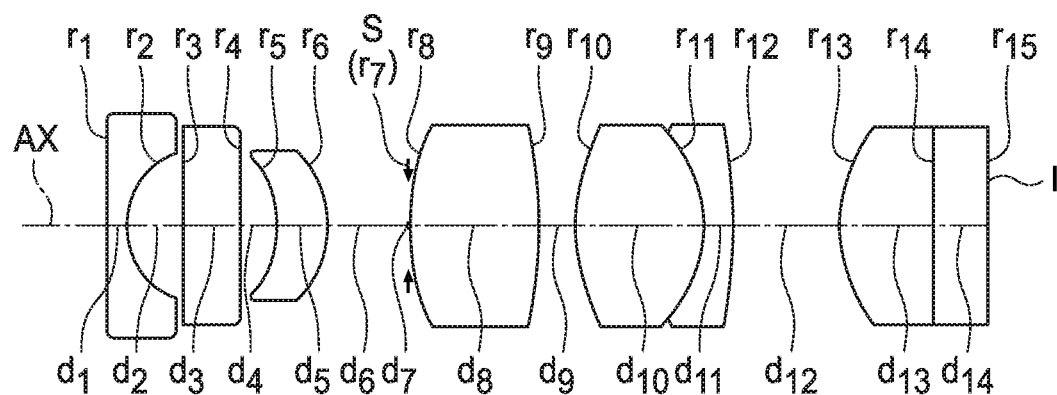
FIG. 2A is a cross-sectional view of a lens arrangement in a normal observation state of an endoscope objective optical system according to an example 1.
Figure 2B:
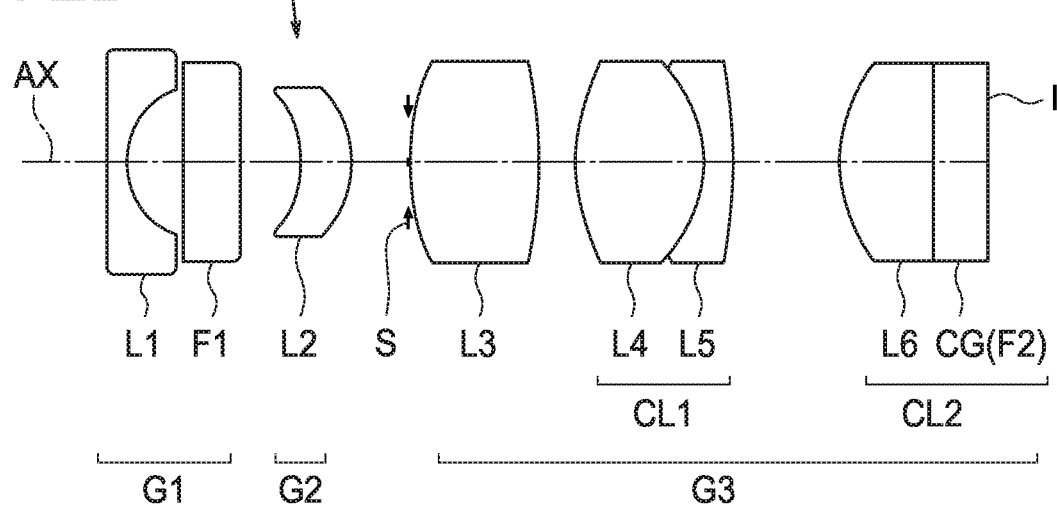
FIG. 2B is a cross-sectional view of a lens arrangement in a close observation state of the endoscope objective optical system according to the example 1.

FIG. 2A is a cross-sectional view of a lens arrangement in a normal observation state of the endoscope objective optical system according to the present example. FIG. 2B is a cross-sectional view of a lens arrangement in a close observation state of the endoscope objective optical system according to the present example.

The endoscope objective optical system includes in order from an object side, a first group G1 having a negative refractive power, a second group G2 having a positive refractive power, an aperture stop S, and a third group G3 having a positive refractive power.

The first group G1 having a negative refractive power includes a first lens L1 which is a planoconcave lens having a negative refractive power of which a flat surface is directed toward the object side, and a plane parallel plate F1. The plane parallel plate F1 is disposed on an image-plane side of the first lens L1 in the first group G1. The second group G2 having a positive refractive power includes a second lens L2 which is a meniscus lens having a positive refractive power of which a convex surface is directed toward an image side.

The second lens L2 which is a meniscus lens having a positive refractive power moves toward the image side (image plane I) along an optical axis AX at the time of focusing from the normal observation state (FIG. 2A) to the close observation state (FIG. 2B).

The third group G3 having a positive refractive power includes a third lens L3 which is a biconvex lens having a positive refractive power, a fourth lens L4 which is a biconvex lens having a positive refractive power, a fifth lens L5 which is a meniscus lens having a negative refractive power of which a convex surface is directed toward the image side, and a sixth lens L6 which is a planoconvex lens having a positive refractive power of which a convex surface is directed toward the object side. The fourth lens L4 having a positive refractive power and the fifth lens L5 having a negative refractive power are cemented, and form a cemented lens CL1.

The aperture stop S is disposed on a front side (object side) of the third group G3. The aperture stop S is fixed to the third group G3 at the time of focusing.

A cover glass CG of a plane parallel plate F2 is affixed to a front surface of an image sensor which is not shown in the diagram. In the present example, the sixth lens L6 is cemented to a front surface (object-side surface) of the cover glass CG, and forms a cemented lens CL2. The sixth lens L6 has a function of a field lens.

The plane parallel plate F' is a filter for cutting specific wavelengths such as, 1060 nm of YAG (yttrium aluminum garnet) laser, 810 nm of semiconductor laser, or an infrared region.

FIG. 3A, FIG. 3B, FIG. 3C, and FIG. 3D show a spherical aberration (SA), an astigmatism (AS), a distortion (DT), and a chromatic aberration of magnification (CC) respectively, in the normal observation state of the present example. FIG. 3E, FIG. 3F, FIG. 3G, and FIG. 3H show a spherical aberration (SA), an astigmatism (AS), a distortion (DT), and a chromatic aberration of magnification (CC) respectively, in the close observation state of the present example.

These aberration diagrams show aberration for each of wavelengths of 656.3 nm (C-line), 486.1 nm (F-line), and 546.1 nm (e-line). Moreover, in the diagrams, 'ω' denotes a half angle of view. Similar reference numerals are used for aberration diagrams below.

Example 2

An endoscope objective optical system according to an example 2 will be described below.

Figure 4A:
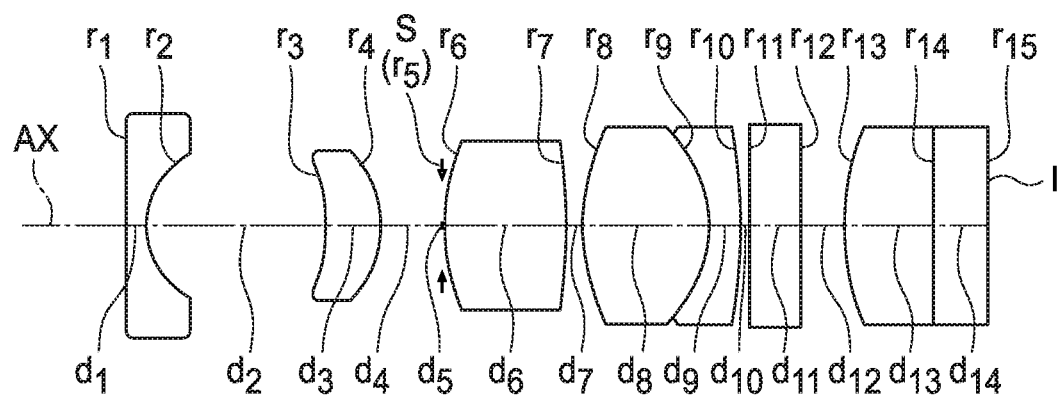
FIG. 4A is a cross-sectional view of a lens arrangement in a normal observation state of an endoscope objective optical system according to an example 2.
Figure 4B:
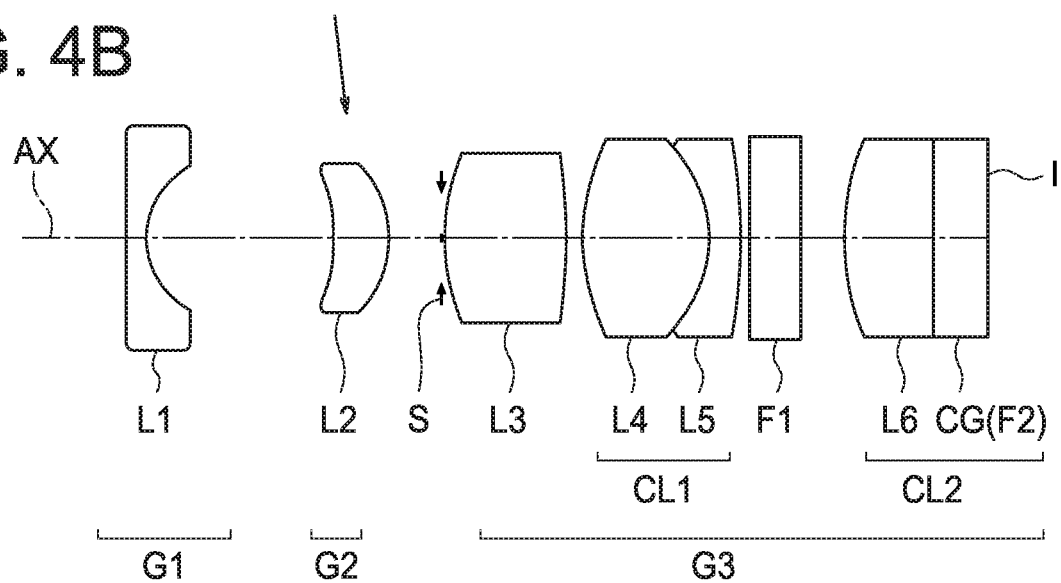
FIG. 4B is a cross-sectional view of a lens arrangement in a close observation state of the endoscope objective optical system according to the example 2.

FIG. 4A is a cross-sectional view of a lens arrangement in a normal observation state of the endoscope objective optical system according to the present example. FIG. 4B is a cross-sectional view of a lens arrangement in a close observation state of the endoscope objective optical system according to the present example.

The endoscope objective optical system includes in order from an object side, a first group G1 having a negative refractive power, a second group G2 having a positive refractive power, an aperture stop S, and a third group G3 having a positive refractive power.

The first group G1 having a negative refractive power includes a first lens L1 which is a planoconcave lens having a negative refractive power of which a flat surface is directed toward the object side. The second group G2 having a positive refractive power includes a second lens L2 which is a meniscus lens having a positive refractive power of which a convex surface is directed toward an image side.

The second lens L2 which is a meniscus lens having a positive refractive power moves toward the image side (image plane I) along an optical axis AX at the time of focusing from the normal observation state (FIG. 4A) to the close observation state (FIG. 4B).

The third group G3 having a positive refractive power includes a third lens L3 which is a biconvex lens having a positive refractive power, a fourth lens L4 which is a biconvex lens having a positive refractive power, a fifth lens L5 which is a meniscus lens having a negative refractive power of which a convex surface is directed toward the image side, and a sixth lens L6 which is a planoconvex lens having a positive refractive power, of which a convex surface is directed toward the object side. The fourth lens L4 having a positive refractive power and the fifth lens L5 which is a meniscus lens having a negative refractive power are cemented, and form a cemented lens CL1.

The aperture stop S is disposed on a front side (object side) of the third group G3. The aperture stop S is fixed to the third group G3 at the time of focusing.

The third group G3 has a plane parallel plate F1 between the cemented lens CL1 and the sixth lens L6. A plane parallel plate F2 is affixed as a cover glass CG to a front surface (image plane I) of an image sensor which is not shown in the diagram. In the present example, the sixth lens L6 is cemented to a front surface (object-side surface) of the cover glass CG, and forms a cemented lens CL2. The sixth lens L6 has a function of a field lens.

The plane parallel plate F1 is a filter for cutting specific wavelengths such as, 1060 nm of YAG laser, 810 nm of semiconductor laser, or an infrared region.

FIG. 5A, FIG. 5B, FIG. 5C, and FIG. 5D show a spherical aberration (SA), an astigmatism (AS), a distortion (DT), and a chromatic aberration of magnification (CC) respectively, in the normal observation state of the present example. FIG. 5E, FIG. 5F, FIG. 5G, and FIG. 5H show a spherical aberration (SA), an astigmatism (AS), a distortion (DT), and a chromatic aberration of magnification (CC) respectively, in the close observation state of the present example.

Example 3

An endoscope objective optical system according to an example 3 will be described below.

Figure 6A:
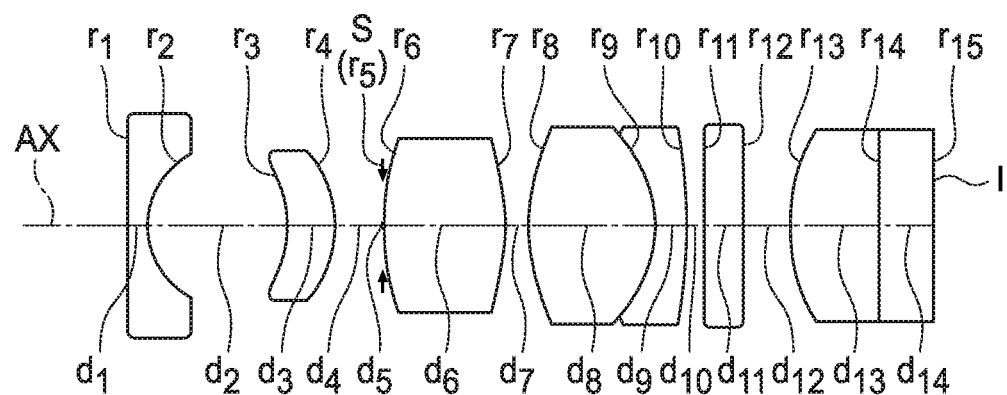
FIG. 6A is a cross-sectional view of a lens arrangement in a normal observation state of an endoscope objective optical system according to an example 3.
Figure 6B:
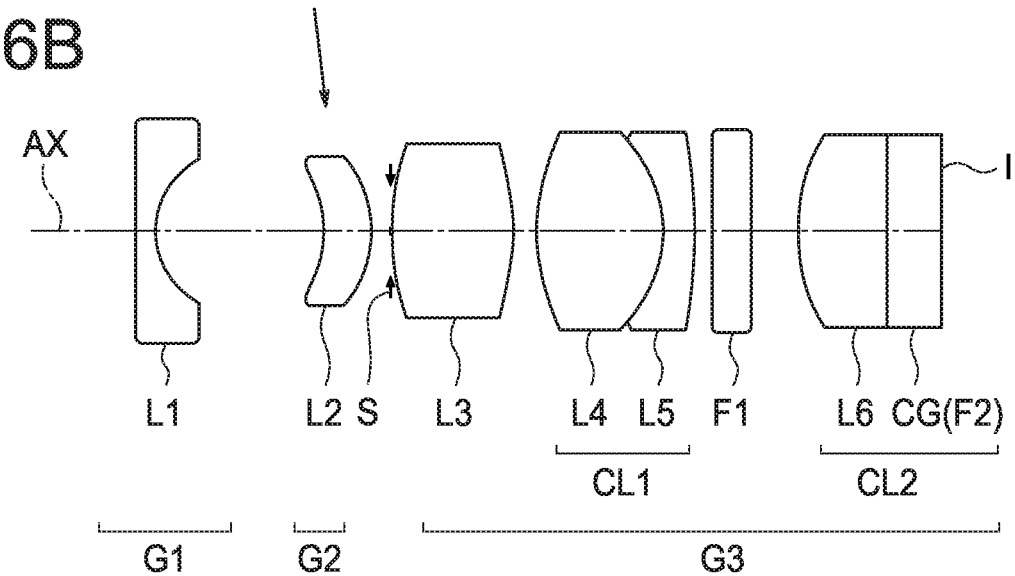
FIG. 6B is a cross-sectional view of a lens arrangement in a close observation state of the endoscope objective optical system according to the example 3.

FIG. 6A is a cross-sectional view of a lens arrangement in a normal observation state of the endoscope objective optical system according to the present example. FIG. 6B is a cross-sectional view of a lens arrangement in a close observation state of the endoscope objective optical system according to the present example.

The endoscope objective optical system includes in order from an object side, a first group G1 having a negative refractive power, a second group G2 having a positive refractive power, an aperture stop S, and a third group G3 having a positive refractive power.

The first group G1 having a negative refractive power includes a first lens L1 which is a planoconcave lens having a negative refractive power of which a flat surface is directed toward the object side. The second group G2 having a positive refractive power includes a second lens L2 which is a meniscus lens having a positive refractive power of which a convex surface is directed toward an image side.

The second lens which is a meniscus lens having a positive refractive power moves toward the image side (image plane I) along an optical axis AX at the time of focusing from the normal observation state (FIG. 6A) to the close observation state (FIG. 6B).

The third group G3 having a positive refractive power includes a third lens L3 which is a biconvex lens having a positive refractive power, a fourth lens L4 which is a biconvex lens having a positive refractive power, a fifth lens L5 which is a meniscus lens having a negative refractive power of which a convex surface is directed toward the image side, and a sixth lens L6 which is a planoconvex lens having a positive refractive power of which a convex surface is directed toward the object side. The fourth lens L4 having a positive refractive power and the fifth lens L5 having which is a meniscus lens having a negative refractive power are cemented, and form a cemented lens CL1.

The aperture stop S is disposed on a front side (object side) of the third group G3. The aperture stop S is fixed to the third group G3 at the time of focusing.

The third group G3 has a plane parallel plate F1 between the cemented lens CL1 and the sixth lens L6. A plane parallel plate F2 is affixed as a cover glass CG to a front surface of an image sensor which is not shown in the diagram. In the present example, the sixth lens L6 is cemented to a front surface (object-side surface) of the cover glass CG, and forms a cemented lens CL2. The sixth lens L6 has a function of a field lens.

The plane parallel plate F1 is a filter for cutting specific wavelengths such as, 1060 nm of YAG laser, 810 nm of semiconductor laser, or an infrared region.

FIG. 7A, FIG. 7B, FIG. 7C, and FIG. 7D show a spherical aberration (SA), an astigmatism (AS), a distortion (DT), and a chromatic aberration of magnification (CC) respectively, in the normal observation state of the present example. FIG. 7E, FIG. 7F, FIG. 7G, and FIG. 7H show a spherical aberration (SA), an astigmatism (AS), a distortion (DT), and a chromatic aberration of magnification (CC) respectively, in the close observation state of the present example.

Example 4

An endoscope objective optical system according to an example 4 will be described below.

Figure 8A:
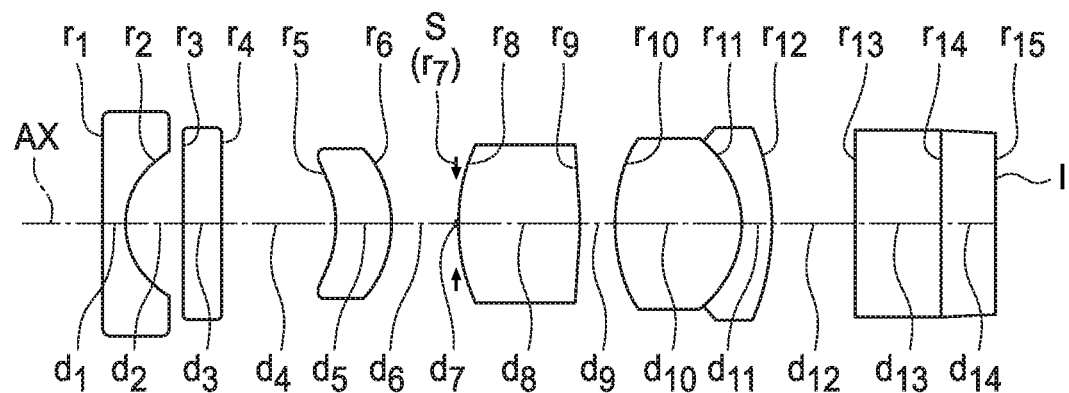
FIG. 8A is a cross-sectional view of a lens arrangement in a normal observation state of an endoscope objective optical system according to an example 4.

FIG. 8A is a cross-sectional view of a lens arrangement in a normal observation state of the endoscope objective optical system according to the present example. FIG. 6B is a cross-sectional view of a lens arrangement in a close observation state of the endoscope objective optical system according to the present example.

The endoscope objective optical system includes in order from an object side, a first group G1 having a negative refractive power, a second group G2 having a positive refractive power, an aperture stop S, and a third group G3 having a positive refractive power.

The first group G1 having a negative refractive power includes a first lens L1 which is a planoconcave lens having a negative refractive power of which a flat surface is directed toward the object side, and a plane parallel plate F1. The plane parallel plate F1 is disposed on an image-plane side of the first lens L1 in the first group G1. The second group G2 having a positive refractive power includes a second lens L2 which is a meniscus lens having a positive refractive power of which a convex surface is directed toward an image side.

Figure 8B:
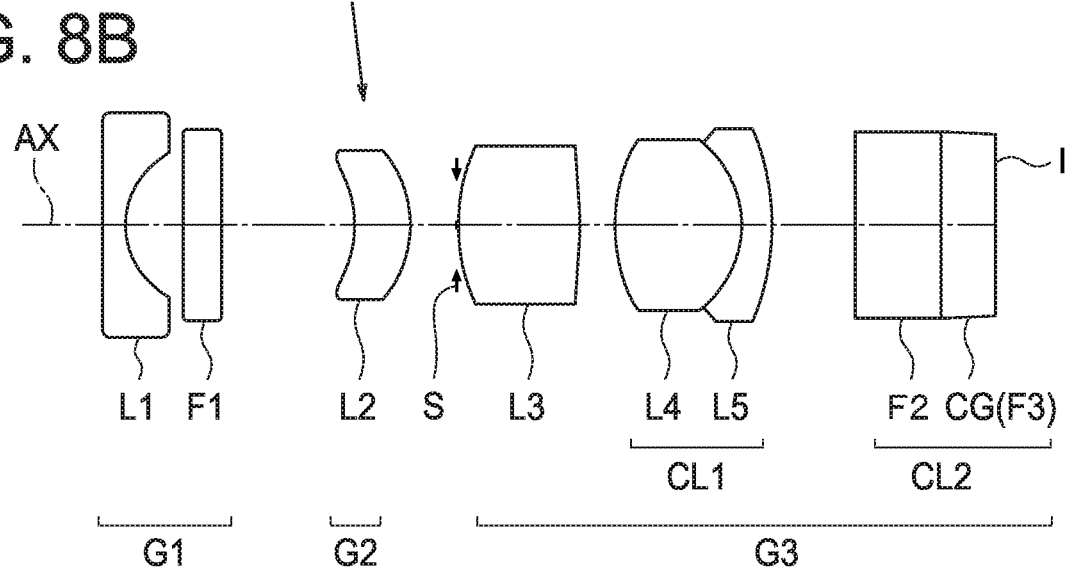
FIG. 8B is a cross-sectional view of a lens arrangement in a close observation state of the endoscope objective optical system according to the example 4.

The second lens L2 which is a meniscus lens having a positive refractive power moves toward the image side (image plane I) along an optical axis AX at the time of focusing from the normal observation state (FIG. 8A) to the close observation state (FIG. 8B).

The third group G3 having a positive refractive power includes a third lens L3 which is a biconvex lens having a positive refractive power, a fourth lens L4 which is a biconvex lens having a positive refractive power, and a fifth lens L5 which is a meniscus lens having a negative refractive power of which a convex surface is directed toward the image side. The fourth lens L4 having a positive refractive power and the fifth lens L5 which is a meniscus lens having a negative refractive power are cemented, and form a cemented lens CL1.

The aperture stop S is disposed on a front side (object side) of the third group G3. The aperture stop S is fixed to the third group G3 at the time of focusing. Moreover, the endoscope objective optical system has on a front surface of the image sensor which is not shown in the diagram, a plane parallel plate F2, and a plane parallel plate F3 as a cover glass CG. The plane parallel plate F2 and the plane parallel plate F3 are cemented, and form a cemented element CL2.

The plane parallel plate F1 is a filter for cutting specific wavelengths such as, 1060 nm of YAG laser, 810 nm of semiconductor laser, or an infrared region.

FIG. 9A, FIG. 9B, FIG. 9C, and FIG. 9D show a spherical aberration (SA), an astigmatism (AS), a distortion (DT), and a chromatic aberration of magnification (CC) respectively, in the normal observation state of the present example. FIG. 9E, FIG. 9F, FIG. 9G, and FIG. 9H show a spherical aberration (SA), an astigmatism (AS), a distortion (DT), and a chromatic aberration of magnification (CC) respectively, in the close observation state of the present example.

Example 5

An endoscope objective optical system according to an example 5 will be described below.

Figure 10A:
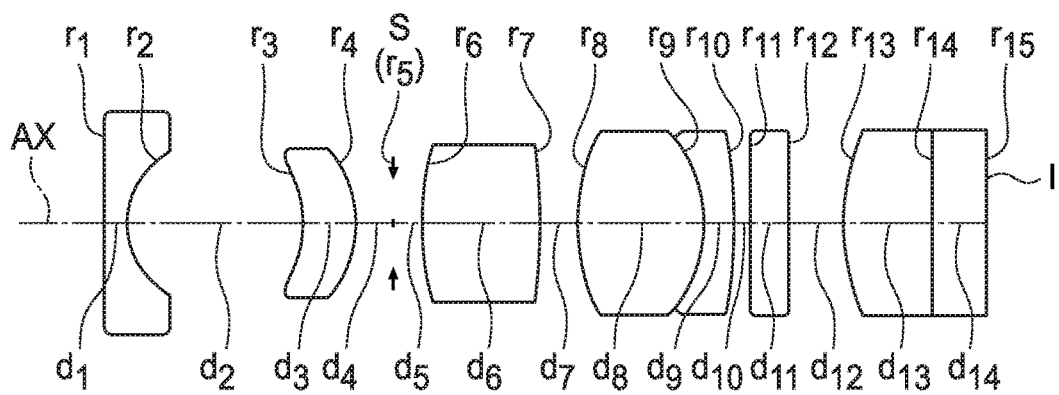
FIG. 10A is a cross-sectional view of a lens arrangement in a normal observation state of an endoscope objective optical system according to an example 5.
Figure 10B:
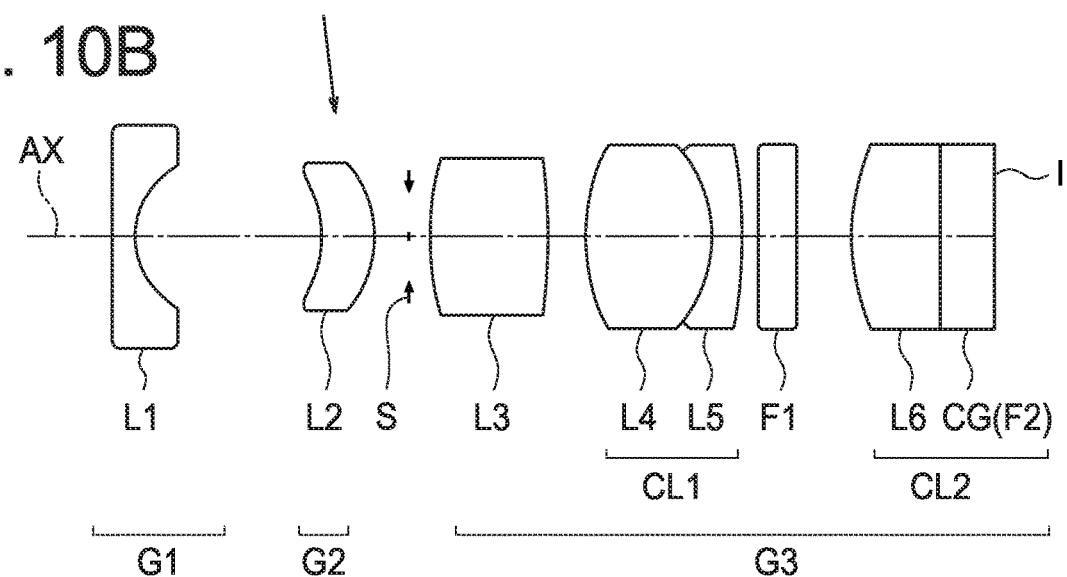
FIG. 10B is a cross-sectional view of a lens arrangement in a close observation state of the endoscope objective optical system according to the example 5.

FIG. 10A is a cross-sectional view of a lens arrangement in a normal observation state of the endoscope objective optical system according to the present example. FIG. 10B is a cross-sectional view of a lens arrangement in a close observation state of the endoscope objective optical system according to the present example.

The endoscope objective optical system includes in order from an object side, a first group G1 having a negative refractive power, a second group G2 having a positive refractive power, an aperture stop S, and a third group G3 having a positive refractive power.

The first group G1 having a negative refractive power includes a first lens L1 which is a planoconcave lens having a negative refractive power of which a flat surface is directed toward the object side. The second group G2 having a positive refractive power includes a second lens L2 which is a meniscus lens having a positive refractive power, of which a convex surface is directed toward an image side.

The second lens L2 which is a meniscus lens having a positive refractive power moves toward the image side (image plane I) at the time of focusing from the normal observation state (FIG. 10A) to the close observation state (FIG. 10B).

The aperture stop S is disposed on the image side (rear side) of the second group G2. The aperture stop S moves toward the image side (image plane I) integrally with the second lens L2 which is a meniscus lens.

The third group G3 having a positive refractive power includes a third lens L3 which is a biconvex lens having a positive refractive power, a fourth lens L4 which is a biconvex lens having a positive refractive power, a fifth lens L5 which is a meniscus lens having a negative refractive power of which a convex surface is directed toward an image side, and a sixth lens L6 which is a planoconvex lens having a positive refractive power of which a convex surface is directed toward the object side. The fourth lens L4 having a positive refractive power and the fifth lens L5 which is a meniscus lens having a negative refractive power are cemented, and form a cemented lens CL1.

The third unit G3 has a plane parallel plate F1 between the cemented lens CL1 and the sixth lens L6. A plane parallel plate F2 is affixed as a cover glass CG to a front surface (image plane I) of an image sensor which is not shown in the diagram. In the present example, the sixth lens L6 is cemented to a front surface (object-side surface) of the cover glass CG, and form a cemented lens CL2. The sixth lens L6 functions as a field lens.

The plane parallel plate F1 is a filter for cutting specific wavelengths such as, 1060 nm of YAG laser, 810 nm of semiconductor laser, or an infrared region.

FIG. 11A, FIG. 11B, FIG. 11C, and FIG. 11D show a spherical aberration (SA), an astigmatism (AS), a distortion (DT), and a chromatic aberration of magnification (CC) respectively, in the normal observation state of the present example. FIG. 11E, FIG. 11F, FIG. 11G, and FIG. 11H show a spherical aberration (SA), an astigmatism (AS), a distortion (DT), and a chromatic aberration of magnification (CC) respectively, in the close observation state of the present example.

Numerical data of each example is shown below. Regarding symbols, r denotes a radius of curvature of each lens surface, d denotes a distance between two lens surfaces, ne denotes a refractive index of each lens for an e-line, vd denotes Abbe's number for each lens, Fno denotes an effective F-number, 2ω denotes a full angle of view, and IH denotes an image height. A stop is an aperture stop.

Example 1

Unit mm

Surface data

| Surface no. | r | d | ne | vd |
|---|---|---|---|---|
| 1 | ∞ | 0.167 | 1.88815 | 40.76 |
| 2 | 0.6092 | 0.4 | | |
| 3 | ∞ | 0.445 | 1.49557 | 75.00 |
| 4 | ∞ | Variable | | |
| 5 | −0.8679 | 0.378 | 1.51825 | 64.14 |
| 6 | −0.85 | Variable | | |
| 7 (Stop) | ∞ | 0.01 | | |
| 8 | 1.9327 | 0.958 | 1.58482 | 40.75 |
| 9 | −3.9801 | 0.274 | | |
| 10 | 1.612 | 0.953 | 1.49846 | 81.54 |
| 11 | −1.1339 | 0.223 | 1.97189 | 17.47 |
| 12 | −4.3605 | 0.802 | | |
| 13 | 1.2968 | 0.7 | 1.51825 | 64.14 |
| 14 | ∞ | 0.4 | 1.507 | 63.26 |
| 15 | Image pickup surface ∞ | | | |

Various data

| | Normal observation state | Close observation state |
|---|---|---|
| Focal length | 0.569 | 0.551 |
| FNO. | 3.12 | 3.11 |
| Object distance | 20 | 3.15 |
| 2ω | 122° | 129.8° |
| IH | 0.5 mm | |
| d4 | 0.26 | 0.4395 |
| d6 | 0.595 | 0.4155 |

Example 2

Unit mm

Surface data

| Surface no. | r | d | ne | vd |
|---|---|---|---|---|
| 1 | ∞ | 0.167 | 1.88815 | 40.78 |
| 2 | 0.5945 | Variable | | |
| 3 | −1.361 | 0.4 | 1.48915 | 70.23 |
| 4 | −0.9493 | Variable | | |
| 5 (Stop) | ∞ | 0.02 | | |
| 6 | 1.7698 | 0.89 | 1.59911 | 39.24 |
| 7 | −9.1185 | 0.133 | | |
| 8 | 1.781 | 0.935 | 1.53947 | 74.70 |
| 9 | −1.07 | 0.222 | 1.97189 | 17.47 |
| 10 | −4.6626 | 0.05 | | |
| 11 | ∞ | 0.4 | 1.49557 | 75.00 |
| 12 | ∞ | 0.321 | | |
| 13 | 2 | 0.67 | 1.51825 | 64.14 |
| 14 | ∞ | 0.38 | 1.507 | 63.26 |
| 15 | Image pickup surface ∞ | | | |

Various data

| | Normal observation state | Close observation state |
|---|---|---|
| Focal length | 0.552 | 0.542 |
| FNO. | 3.02 | 3.02 |
| Object distance | 11.7 | 4.75 |
| 2ω | 129.2° | 132.6° |
| IH | 0.5 mm | |

-continued

| Unit mm | | |
|---|---|---|
| d2 | 1.317 | 1.3745 |
| d4 | 0.4615 | 0.404 |

Example 3

| Unit mm | | | | |
|---|---|---|---|---|
| Surface data | | | | |
| Surface no. | r | d | ne | vd |
| 1 | ∞ | 0.16 | 1.88815 | 40.78 |
| 2 | 0.6283 | Variable | | |
| 3 | −0.9625 | 0.356 | 1.48915 | 70.23 |
| 4 | −0.9532 | Variable | | |
| 5 (Stop) | ∞ | 0.02 | | |
| 6 | 2.1367 | 0.89 | 1.58482 | 40.75 |
| 7 | −2.1367 | 0.18 | | |
| 8 | 1.6271 | 0.935 | 1.49846 | 81.54 |
| 9 | −1.0356 | 0.223 | 1.97189 | 17.47 |
| 10 | −4.1943 | 0.132 | | |
| 11 | ∞ | 0.3 | 1.523 | 65.13 |
| 12 | ∞ | 0.33 | | |
| 13 | 1.38 | 0.67 | 1.51825 | 64.14 |
| 14 | ∞ | 0.3898 | 1.507 | 63.26 |
| 15 | Image pickup surface ∞ | | | |

| Various data | | |
|---|---|---|
| | Normal observation state | Close observation state |
| Focal length | 0.552 | 0.533 |
| FNO. | 4.07 | 4.07 |
| Object distance | 11.75 | 3.11 |
| 2ω | 127.6° | 135.9° |
| IH | 0.5 mm | |
| d2 | 1.013 | 1.222 |
| d4 | 0.347 | 0.138 |

Example 4

| Unit mm | | | | |
|---|---|---|---|---|
| Surface data | | | | |
| Surface no. | r | d | ne | vd |
| 1 | ∞ | 0.17 | 1.88815 | 40.78 |
| 2 | 0.6692 | 0.4 | | |
| 3 | ∞ | 0.33 | 1.49557 | 75.00 |
| 4 | ∞ | Variable | | |
| 5 | −0.9478 | 0.4 | 1.51825 | 64.14 |
| 6 | −0.9478 | Variable | | |
| 7 (Stop) | ∞ | 0.02 | | |
| 8 | 1.6435 | 0.88 | 1.58482 | 40.75 |
| 9 | −31.7941 | 0.285 | | |
| 10 | 1.2698 | 0.935 | 1.48915 | 70.23 |
| 11 | −0.8328 | 0.223 | 1.93429 | 18.90 |
| 12 | −2.1041 | 0.61 | | |
| 13 | ∞ | 0.65 | 1.51825 | 64.14 |
| 14 | ∞ | 0.38 | 1.507 | 63.26 |
| 15 | Image pickup surface ∞ | | | |

| Various data | | |
|---|---|---|
| | Normal observation state | Close observation state |
| Focal length | 0.557 | 0.543 |
| FNO. | 3.53 | 3.52 |

-continued

| Unit mm | | |
|---|---|---|
| Object distance | 12 | 4.67 |
| 2ω | 127.1° | 131.3° |
| IH | 0.5 mm | |
| d4 | 0.842 | 0.952 |
| d6 | 0.4636 | 0.3535 |

Example 5

| Unit mm | | | | |
|---|---|---|---|---|
| Surface data | | | | |
| Surface no. | r | d | ne | vd |
| 1 | ∞ | 0.17 | 1.88815 | 40.78 |
| 2 | 0.6126 | Variable | | |
| 3 | −1.104 | 0.4 | 1.51825 | 64.14 |
| 4 | −0.9344 | 0.2633 | | |
| 5 (Stop) | ∞ | Variable | | |
| 6 | 2.0151 | 0.88 | 1.58482 | 40.75 |
| 7 | −5.2097 | 0.282 | | |
| 8 | 1.7505 | 0.935 | 1.53947 | 74.70 |
| 9 | −1.1756 | 0.22 | 1.97189 | 17.47 |
| 10 | −4.733 | 0.12 | | |
| 11 | ∞ | 0.3 | 1.523 | 65.13 |
| 12 | ∞ | 0.416 | | |
| 13 | 2 | 0.66 | 1.51825 | 64.14 |
| 14 | ∞ | 0.4 | 1.507 | 63.26 |
| 15 | Image pickup surface ∞ | | | |

| Various data | | |
|---|---|---|
| | Normal observation state | Close observation state |
| Focal length | 0.553 | 0.543 |
| FNO. | 3.35 | 3.39 |
| Object distance | 11.8 | 4.67 |
| 2ω | 129° | 132.9° |
| IH | 0.5 mm | |
| d2 | 1.31 | 1.381 |
| d5 | 0.22 | 0.149 |

Values of the conditional expressions (1) to (6) of each of the embodiments are shown below.

| Conditional Expression | Example 1 | Example 2 | Example 3 |
|---|---|---|---|
| (1) G2f/FL | 17.041 | 8.812 | 26.924 |
| (2) G1f/G2f | −0.071 | −0.138 | −0.048 |
| (3) (R3 − R4)/(R3 + R4) | 0.010 | 0.178 | 0.005 |
| (4) V2/FL | 0.316 | 0.104 | 0.379 |
| (5) f31/f32 | −0.925 | −0.950 | −0.981 |
| (6) G3f/FL | 3.656 | 3.395 | 3.136 |

| Conditional Expression | Example 4 | Example 5 |
|---|---|---|
| (1) G2f/FL | 22.796 | 11.755 |
| (2) G1f/G2f | −0.059 | −0.106 |
| (3) (R3 − R4)/(R3 + R4) | 0.000 | 0.083 |
| (4) V2/FL | 0.198 | 0.128 |
| (5) f31/f32 | −0.747 | −0.884 |
| (6) G3f/FL | 3.056 | 3.497 |

Various embodiments of the disclosure have been described heretofore. However, the disclosure is not restricted to the embodiments described heretofore, and embodiments in which arrangements of these embodiments are combined appropriately without departing from the scope of the disclosure are also in the scope of the disclosure.

The abovementioned endoscope objective optical system and endoscope may satisfy a plurality of arrangements simultaneously. Doing so is preferable for achieving a favorable endoscope objective optical system. Moreover, the combinations of preferable arrangements are arbitrary. Furthermore, regarding conditional expressions, only an upper limit value or a lower limit value of a numerical range of more restricted conditional expression may be restricted.

(Note)

A disclosure of following arrangements is derived from the examples described above.

(Appended Mode 1)

An endoscope objective optical system comprising in order from an object side:
a first group having a negative refractive power;
a second group having a positive refractive power; and
a third group having a positive refractive power, wherein
focusing from an object point at a long distance to an object point at a short distance is carried out by moving the second group from the object side to an image side, the first group includes a first lens having a negative refractive power, the second group includes a second lens which is a meniscus lens having a positive refractive power of which a convex surface is directed toward the image side, and the third group includes in order from the object side, a third lens having a positive refractive power, and a cemented lens in which a fourth lens having a positive refractive power and a fifth lens having a negative refractive power are affixed.

(Appended Mode 2)

The endoscope objective optical system according to appended mode 1, wherein at least one of following conditional expressions (1), (2), (3), and (4) is satisfied $$8 < G2f/FL < 35 \qquad (1)$$

$$-0.16 < G1f/G2f < -0.04 \qquad (2)$$

$$0 \leq (R3-R4)/(R3+R4) < 0.2 \qquad (3)$$

$$0.1 < V2/FL < 0.4 \qquad (4)$$

where,

FL denotes a focal length of the overall endoscope objective optical system at the time of a far-point observation, G1f denotes a focal length of the first group, G2f denotes a focal length of the second group, R3 denotes a radius of curvature of an object-side surface of a lens in the second group, R4 denotes a radius of curvature of an image-side surface of a lens in the second group, and V2 denotes an amount of movement of the second group (at the time of focusing from an object point at a long distance to an object point at a short distance).

(Appended Mode 3)

The endoscope objective optical system according to one of appended modes 1 and 2, wherein at least one of following conditional expressions (5) and (6) is satisfied $$-1.2 < f31/f32 < -0.7 \qquad (5)$$

$$2.5 < G3f/FL < 4.5 \qquad (6)$$

where, f31 denotes a focal length of a lens having a positive refractive power which forms the cemented lens in the third group, f32 denotes a focal length of a lens having a negative refractive power which forms the cemented lens in the third group, G3f denotes a focal length of the third group, and FL denotes the focal length of the overall endoscope objective optical system at the time of the far-point observation.

As described heretofore, the disclosure is appropriate for an endoscope objective optical system and an endoscope having a shortened overall length, a small outer diameter, and a favorable optical performance, and on which, a focusing mechanism (lens moving mechanism) can be installed.

According to the disclosure, it is possible to provide an endoscope objective optical system having a shortened overall length, a small outer diameter, and a favorable optical performance, and on which, a focusing mechanism (lens moving mechanism) can be installed, and an endoscope using the same.

What is claimed is:

1. An endoscope objective optical system comprising, in order from an object side:

a first group having a negative refractive power;

a second group having a positive refractive power; and a third group having a positive refractive power, wherein:

focusing from an object point at a long distance to an object point at a short distance is carried out by moving the second group from the object side to an image side, the first group includes only one lens and a parallel plate filter, the one lens having a negative refractive power, and the parallel plate filter being provided on the image side of the one lens, the second group includes a lens which is a meniscus lens having a positive refractive power of which a convex surface is directed toward the image side, the third group includes, in order from the object side, a lens having a positive refractive power, and a cemented lens composed of a lens having a positive refractive power and a lens having a negative refractive power, and the following conditional expressions (1″), (2), (3), and (4) are satisfied:

$$8 < G2f/FL \leq 17.041 \qquad (1″)$$

$$-0.16 < G1f/G2f < -0.04 \qquad (2)$$

$$0 \leq (R3-R4)/(R3+R4) < 0.2 \qquad (3)$$

$$0.1 < V2/FL < 0.4 \qquad (4)$$

where,

FL denotes an overall focal length of the endoscope objective optical system at a time of a far-point observation, G1f denotes a focal length of the first group, G2f denotes a focal length of the second group, R3 denotes a radius of curvature of an object-side surface of the meniscus lens, R4 denotes a radius of curvature of an image-side surface of the meniscus lens, and V2 denotes an amount of movement of the second group at a time of focusing from the object point at the long distance to the object point at the short distance.

2. An endoscope comprising:

the endoscope objective optical system according to claim 1.

* * * * *